United States Patent [19]
Naveh

[11] Patent Number: 5,877,154
[45] Date of Patent: Mar. 2, 1999

[54] PHARMACEUTICAL COMPOSITIONS FOR THE TREATMENT OR PREVENTION OF DISORDERS IN THE EYE

[75] Inventor: Nava Naveh, Tel-Aviv, Israel

[73] Assignee: Ramot University Authority for Applied Research and Industrial Development Ltd., Tel-Aviv, Israel

[21] Appl. No.: 570,813

[22] Filed: Dec. 12, 1995

Related U.S. Application Data

[63] Continuation of Ser. No. 38,109, Mar. 29, 1993, abandoned.

[30] Foreign Application Priority Data

Apr. 1, 1992 [IL] Israel ......................................... 101441

[51] Int. Cl.⁶ ..................................................... A61K 38/00
[52] U.S. Cl. ............................................. 514/14; 530/517
[58] Field of Search ................................ 530/517; 514/14

[56] References Cited

FOREIGN PATENT DOCUMENTS

| 0146113 | 6/1985 | European Pat. Off. . |
|---|---|---|
| 0234855 | 9/1987 | European Pat. Off. . |
| 3623019 | 1/1988 | Germany . |

OTHER PUBLICATIONS

T. Hanaoka, "Effect of Melanophore Hormone on Regeneration of Visual Purple in Solution", Nature, vol. 172, 1953, p. 866.

O.G. Stroeva et al., "A Hormone–Sensitive Stage in Development of the Retinal Pigment Epithelium in the Hunter Rats with Inherited Retinal Distrophy", Ontogenez, vol. 19, No. 1, 1988, pp. 30–36.

Benelli, et al, *Europ. Journal of Pharmacology*, 150 211–219, 1988.

Hiltz, et al, *Peptides*, vol. 12, pp. 769–771, 1991.

Eberle, A.N., Karger Press, 1988, pp. 336–337, 346–349, 459–461.

*Primary Examiner*—Cecilia J. Tsang
*Assistant Examiner*—Jennifer Harle
*Attorney, Agent, or Firm*—Helfgott & Karas, PC.

[57] ABSTRACT

Eye diseases or disorders are treated by an active agent being a melanotropin peptide or an analogue thereof, the analogue being an agent having a biological effect resembling that of the melanotropin peptide. The active agent may be administered topically onto the eye, by injection into the eye or systemically.

14 Claims, 8 Drawing Sheets

PHARMACEUTICAL COMPOSITIONS FOR THE TREATMENT OR PREVENTION OF DISORDERS IN THE EYE

This is a continuation, of application Ser. No. 08/038,109, filed Mar. 29, 1993, now abandoned.

FIELD OF THE INVENTION

The present invention concerns the treatment of age related or other eye disorders. More specifically, the present invention concerns treatment of various eye disorders by the use of melantropin peptides such as α-MSH or analogues thereof.

BACKGROUND OF THE INVENTION

Age related degenerative changes in the eye's retina pigment epithilium (RPE), a highly pigmented epithilium underlying the retina, occur mainly in the macula area. Since the macula is the area which enables to discern small details and to read, its deterioration may bring about visual impairment and even blindness. Age related changes of varying degrees in the macula are evident in about 10% of subjects over 50 and about 25% of subjects over 75. One of the main factors responsible for age related macular degeneration (AMD) is aging of the Retinal Pigment Epithelium (RPE) at the macular area. In the intact eye, the RPE cells, through their phagocytic activity and active metabolism, constantly remove the toxic metabolites produced by the overlaying photoreceptoric retinal cells during the visual transduction process.

As a consequence of the age dependent reduction in the metabolic and pharmaceutical activity of cells of the RPE, metabolic waste products are accumulated within these cells causing a slow deterioration of the activity of the RPE cells and their death. This deterioration, and death of cells occurs mainly in the macula region, eventually causes the degradation of the overlaying retinal layer and photoreceptors with subsequent impairment of vision or even blindness.

Although AMD is the most prevalent cause of blindness in the elder population in developed countries, there is to date no effective treatment available to prevent the development of AMD or to ameliorate the condition following the onset of this disorder.

Melanotropin (alpha melanocytic stimulating hormone (α-MSH)) is an N-Acetyl-tridecapeptide hormone which is synthesized and secreted by the intermediate lobe of the pituitary gland, and is known to control skin pigmentation in many animals by stimulating melanin synthesis and movement within integumental melanocytes. Recently, melanotropin has been also reported to affect other physiological functions including: endocrine and exocrine gland activities, temperature regulation, immuno modulation and nerve regeneration. Cellular responses to melanotropin in cultured melanoma cells include elevation of c-AMP levels, increase in melanin synthesis and stimulation of cell proliferation.

Melanotropin was found to have also various effects on the eye. This hormone causes the acceleration of the regeneration of retinal visual purple both in vivo and in vitro and increases light sensitivity (Hanoka, 1953); it was also found to stimulate the melanin synthesis in the RPE of rats with inherited retinal dystrophy (Stroeva and Bibikova, 1988). In addition, this hormone was found to increase the release of retinal neurotransmitters, especially dopamine and GABA (Bauer and Ehringer, 1980). Recently it has been found that melanotropin enhances eicosanoid production by bovine RPE in organ culture without any effect on other retinal layers (Bar-Ilan et al., 1992).

Derivatives of this naturally occurring tridecapeptide in which one or more amino acids has been replaced by another are well known. Some of these derivatives are more stable than the native protein, and others, such as Nle$^4$D-Phe$^7$ α-MSH were found to be more potent than the native peptide in affecting various biological phenomenon (Dayes et al., 1987). Sawyer et al. (Sawyer et al. 1990) have established the fact that only a few amino acids are sufficient to cause the full biological activity of the native protein.

SUMMARY OF THE INVENTION

In accordance with the invention, various eye diseases or disorders, especially those related to the retina and macula are treated by the use of an active agent being a melanotropin peptide or an analogue thereof, the analogue being an agent having a biological effect resembling that of the melanotropin peptide.

Melanotropin peptides may be melanotropin (α-MSH), β-MSH, γ-MSH, lipotropins of the β and γ type, etc. In addition, melanotropin peptides include also antagonists of the aforementioned peptides such as melanocytic concentrating hormone (MCH) which is a physiological antagonist of melanotropin.

The analogues of the melanotropin peptides comprise agents which are capable of binding to melanotropin peptides' receptors, agents capable of increasing the level of the second messenger of such receptors, e.g. activating the enzymatic pathway by which the second messenger is produced, they may be a permeable analogue of the second messenger, or may also be a substance capable of mimicking or modulating the activation of the target of the second messenger.

Examples of the above analogues are derivatives of the melanotropin peptides which do not substantially reduce or at times increase the biological activity of the native peptide or increase duration of activity such as active fragments of melanotropin peptides (see Benelli et al 1988, Johnston et al. 1983, and Hadley and Dawson 1988)); melanotropin peptides or said fragments in which one or more amino acid has been deleted, replaced or chemically modified without substantially reducing the biological activity of the peptide or fragments thereof.

Currently preferred active agents in accordance with the invention include melanotropin, which is an N-acetyl-tridecapeptide having the sequence of Ac-Ser-Tyr-Ser-Met-Glu-His-Phe-Arg-Trp-Gly-Lys-Pro-Val-NH$_2$(SEQ ID NO. 1), and analogues thereof. Examples of these analogues are peptides having a similar tertiary structure in the receptor-binding domain. A particular example of such an analogue is Nle$^4$D-Phe$^7$ α-MSH.

The present invention provides a pharmaceutical composition for the treatment of eye diseases or disorders, comprising an effective amount of said active agent and a pharmaceutically acceptable carrier.

The invention also provides a method for the treatment of eye diseases or disorders comprising administering to the subject in need an effective amount of a melanotropin peptide or an analgoue thereof.

The invention still further provides use of a melanotropin peptide for the preparation of a pharmaceutical composition for the treatment of eye diseases or disorders.

In accordance with one embodiment of the invention, said active agent is administered to individuals in order to induce the active metabolism of RPE cells. Induction of active metabolism in these cells may counter age related deterioration of the RPE, which may in turn reverse or avoid deterioration of the cells in the retinal layer. Consequently, in accordance with the said one embodiment, said active agent is administered to individuals for preventing or ameliorating degenerative changes in the eye, such as those resulting from age related changes in the retina, as well as other retinal dystrophies such as Retinitis-Spigmentosa and Familial macular degeneration.

In accordance with a second embodiment of the invention, melanotropin is administered to individuals for the purpose of inducing migration of RPE cells. Such induced migration may be effective in treating various eye injuries by covering areas devoid of active RPE cells.

In accordance with a third embodiment of the invention, melanotropin is administered to individuals in order to reduce intraocular pressure (IOP), such as in the case of glaucoma.

In accordance with a fourth embodiment of the invention, melanotropin is administered to individuals in order to inhibit inflammatory reactions or surgical trauma in the cornea and other parts of the eye.

Said active agent may be formulated for administration in a large number of ways. One mode of administration of said active agent is topically. For topical application, said active agent is formulated with a vehicle which enables penetration of said active agent into the eye.

Another mode of administration of said active agent is by periocular or intraocular injection. This mode of application is particularly applicable for the treatment of eye inflammations as well as retinal disorders. Periocular injection involves an injection of the drug either into the conjunctiva or to the tennon (fibrous tissue overlaying the eye). This mode of injection is currently routinely used, e.g. following glaucoma surgery or in endophtalmitis—an intraocular inflammation. In intraocular injection, said active agent is injected into the vitreous. This kind of injection is used routinely in cases of severe inflammatory conditions of the eye. Such injection may suitably be given, depending on the clinical status, once every 3 to 6 months.

Another mode of administration of said active agent is systemically, i.e. orally or parenterally or transdermally.

Depending on the mode of administration, the pharmaceutical compositions of the present invention can be in the form of tablets or capsules suitable for oral administration; in the form of a saline solution or any other suitable liquid for subconjunctival injection or for parenteral systemic administration; in the form of powder for the preparation of such liquids; in the form of eye drops or eye ointments suitable for topical administration to the eye and in the form of liposomes or other slow release systems for periocular or intraocular injections.

The invention will in the following be described with reference to some non-limiting examples with occasional reference to the drawings.

BRIEF DESCRIPTION OF THE DRAWINGS

FIG. 7(*a*) shows the amount of leukotriene LTB$_4$ (pg/mg weight) produced by nonirradiated eyes of rats from three experimental groups: (1) untreated; (2) treated I.P. with 4 mg/kg per day of dexamethasone; and (3) treated with I.P. 10 μg/kg per day of melanotropin;

FIG. 7(*b*) shows the amount of leukotriene B$_4$ (LTB$_4$) produced by inflamed eyes of the same three groups of rats in FIG. 7(*a*), the inflammation being induced by exposure of the eyes to UV irradiation prior to the treatment; and FIGS. 8(*a*) and 8(*b*) show the amount of prostaglandin E$_2$ (PGE$_2$) (pg/mg weight) in the same eyes of FIGS. 7(*a*) and 7(*b*), respectively.

EXAMPLES

EXAMPLE 1

The effect of melanotropin on human retinal pigment epithelium cell culture

Cell cultures were obtained from post-mortem human adult eyes no more than 24 hours after death. The eyes were obtained from Tel-Hashomer Eye Bank (Tel-Hashomer Hospital, Israel) after removal of the cornea. The eyes were left in a sterile environment overnight at 4° C. before they were processed. The vitreous and neurosecretory retina were then separated and removed from the RPE. The posterior segment of the globe was filled with 1.25% trypsin—0.05% EDTA solution and allowed to incubate for 45 mins. at 37° C. and 10% CO$_2$ incubator before harvesting the RPE.

The RPE cells were added to complete medium composed of Hams F-10 nutrient mixture (Biological Industries, Beth HaEmek, Israel), 15% of heat inactivated fetal calf serum (FCS), 2 mM glutamine, 100 U/ml penicillin B, 0.1 mg/ml streptomycin and 2.5 ug/ml amphotericin B, and 4.5 g/l glucose (all ingredients from Biological Industries, Kibbutz Beth Haemek, Israel). Cells were centrifuged for five minutes at 1000 RPM and then resuspended in the complete medium. The cells were grown on 25 cm² tissue culture dishes (Nunc, Denmark) at 37° C., in a 10% $CO_2$ humidified atmosphere and the medium was changed twice a week.

RPE cells at confluence (after four-five passages) were lightly trypsinized and then plated in 24-well plates (Cell-Cult, Sterilin, England) at a concentration of $6\times10^4$ cells per well in a complete medium. The cells were grown 3 to 4 days until complete confluence and then the wells containing these cells were filled with phosphate buffered saline (PBS).

The wells were then divided into five groups and a different medium was added to the wells of each group: to the first group, $10^{-6}M$ of melanotropin in serum-free Hams F-10 complete medium was added; to the second group, $10^{-7}M$ of melanotropin in the same medium was added; to the third group 10 ng/ml of Epidermal growth factor (EGF) in the same medium was added; to the fourth group 9 ng/ml basic fibroblast growth factor (bFGF) in the same medium was added; and in the last group serving as control, only the serum-free medium was added.

Cells were incubated for 18 hours at 37° C. in a 10% $CO_2$ incubator with the above medium and then pulsed with 2 µCi/ml of ³H-Thymidine (NEN Research Products, DuPont, Wilmington, Del., U.S.A.) for 2 hours. The cells were washed three times with PBS and five times with ice cold 5% trichloracetic acid. 1 ml of 0.1N NaOH containing 0.1% sodium dodecyl sulphate was added. After 1 hour a 100 µl aliquot was withdrawn from each well, put into 4.5 ml of scintillation fluid and counted after one hour in a Liquid Scintillation Analyzer (Packard, Canberra, Australia).

Figure 1:
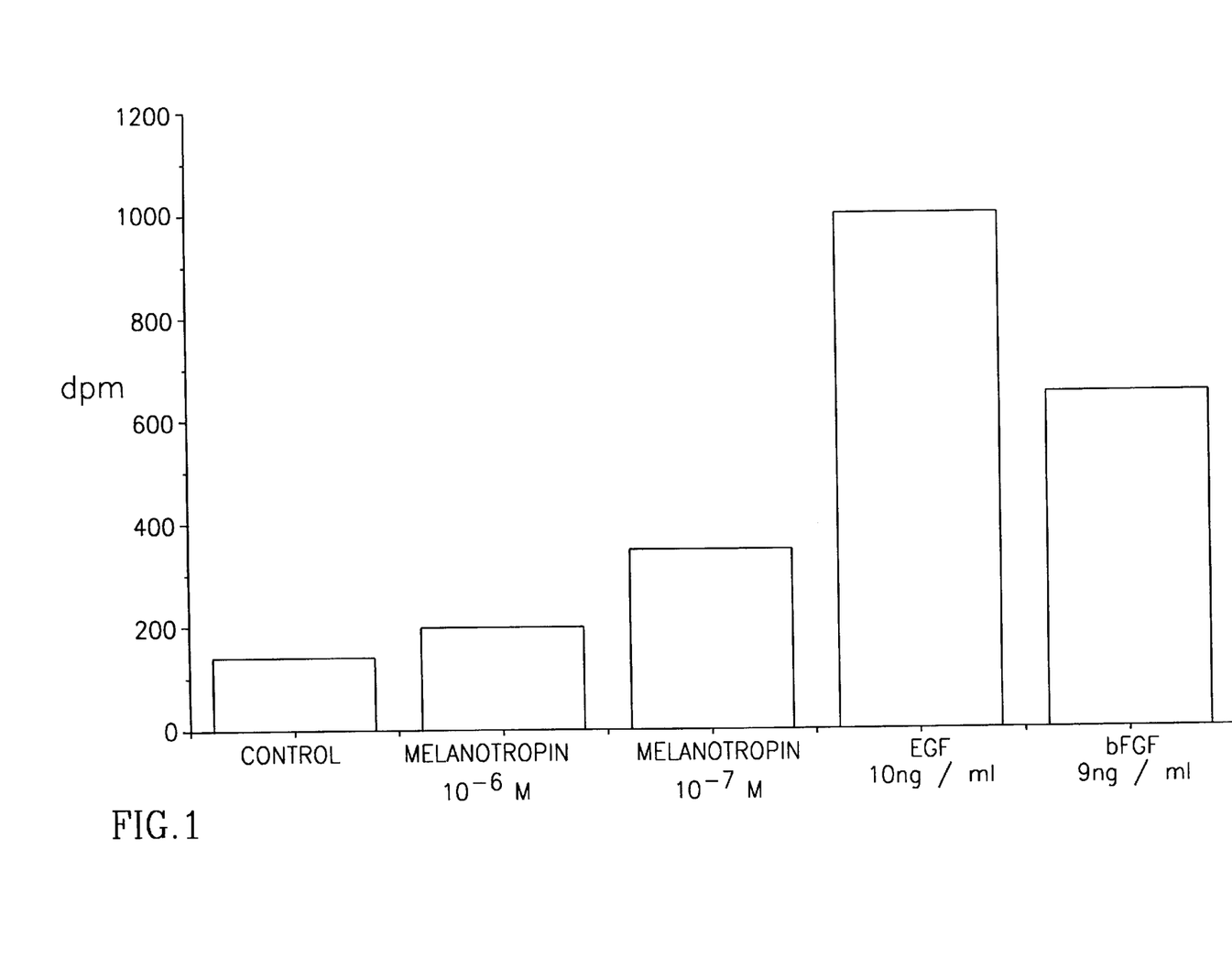
FIG. 1 shows the decomposition per minute of $^3$H-Thymidine from five cultures of Thymidine-labelled RPE cells, each incubated with a different growth factor: basic fibroblast growth factor (bFGF), Epidermal growth factor (EGF), melanotropin at concentrations of $10^{-6}$M and $10^{-7}$M and a control medium.

Triplicate counts were made and the mean and standard deviation of each preparation are shown in FIG. 1 (results are in decomposition per minute).

As can be seen in FIG. 1, melanotropin caused a dose related increase in thymidine uptake by cultured RPE cells which was significantly lower than that elicited by EGF and bFGF.

bFGF and EGF are unsuitable as therapeutic agents for enhancing the metabolic activity of RPE cells as their action is non-selective affecting also fibroblastic and macrophagic elements in the retina leading to scar formation in the retina (Baird et al., 1985).

The amount of RPE cellular proliferation following the addition of melanotropin was significantly smaller than that exerted by bFGF or EGF indicating that this hormone will not be associated with scar formation but may rather selectively augment the RPE cells' metabolic activity.

EXAMPLE 2

The effect of melanotropin on human skin fibroblast (HSF) cell culture

HSF cells were grown in DMEM (Dulbeccos Modified Eagles Media) supplemented with 10% heat inactivated fetal calf serum, 2 mM glutamine and antibiotics (100 U/mi penicillin G, 0.25 mg/ml amphotericin B and 0.1 mg/ml streptomycin) (Biological Industries, Beth Haemek, Israel) in 56.7 cm² tissue culture flasks (Nunc, Roskilde, Denmark) at 37° C. in a 10% $CO_2$ humidified atmosphere incubator. When the cells reached confluency, they were tripsinized by incubation with 0.083% tripsine (Biological Industries, Beth HaEmek, Israel) for a few minutes at 37° C. and seeded (please complete). The growth medium of the cells with or without drugs was changed twice a week.

The wells were then divided into five groups and a different medium was added to the wells of each group as described in Example 1. The medium added to each of the five groups was: (1) serum free medium containing melanotropin $10^{-6}M$; (2) serum free medium containing melanotropin $10^{-7}M$; (3) serum free medium containing EGF 10 ng/ml; (4) serum free medium containing bFGF 9 nn/ml; and (5) serum free medium only.

The degree of ³H-Thymidine uptake by human skin fibroblast was determined as described in Example 1.

Figure 2:
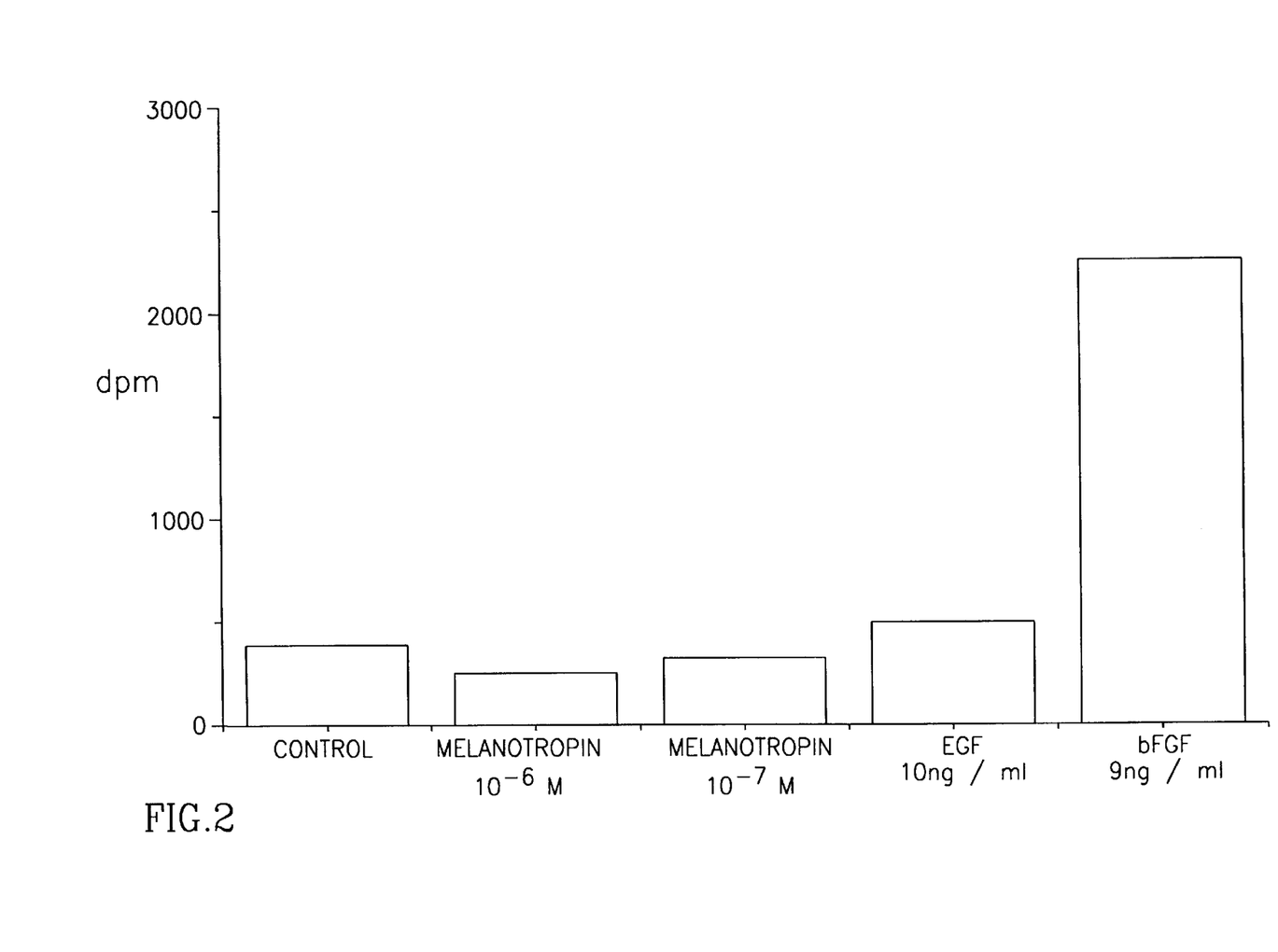
FIG. 2 shows the decomposition per minute of $^3$H-Thymidine from five cultures of human skin fibroblast cells, each incubated with a different growth factor: basic fibroblast growth factor (bFGF), Epidermal growth factor (EGF), melanotropin at concentrations of $10^{-6}$M and $10^{-7}$M and a control medium.

As seen in FIG. 2, only the addition of bFGF to the human skin fibroblasts caused a five-fold increase in ³H-Thymidine uptake as compared to the ³H-Thymidine uptake of cells treated with medium alone. The addition of EGF and melanotropin did not cause any increase in Thymidine uptake by the cells. (The fact that EGF had no effect on the ³H-Thymidine uptake of the human skin fibroblast was not surprising due to the known fact that EGF is incapable of inducing proliferation of fibroblast obtained from other organs as well).

EXAMPLE 3

The effect of melanotropin on bovine vascular endothilial cells (ABAE)

ABAE cells were grown in DMEM (Dulbeccos Modified Eagles Media) supplemented with 5% heat inactivated fetal calf serum, 5% heat inactivated newborn calf serum, 2 mM glutamine and antibiotics (100 U/ml penicillin G, 0.25 mg/ml amphotericin B and 0.1 mg/ml streptomycin) (all from Biological Industries, Beth HaEmek, Israel) in 56.7 cm² tissue culture dishes (Nunc, Roskilde, Denmark) at 37° C. in a humidified atmosphere incubator with 10% $CO_2$.

The cultures were supplemented every other day with $10^{-9}$ ng/ml of bFGF until they reached confluency.

The cells were then trypsinized by adding 0.041% trypsin (Biological Industries, Beth HaEmek, Israel) for a few minutes at 37° C. The cells were then diluted by a factor of six and plated in microwell plates. Growth medium was changed twice a week.

The cells were then divided into five groups as described in Examples 1 and 2 and a different medium was added to the wells of each group as follows: (1) serum free medium containing melanotropin $10^{-6}M$; (2) serum free medium containing melanotropin $10^{-7}M$; (3) serum free medium containing EGF 10 ng/ml; (4) serum free medium containing bFGF 9 ng/ml; and (5) serum free medium alone.

The degree of ³H-Thymidine uptake by the cells was again determined as described in Examples 1 and 2.

A single set of experiments was carried out with these cells and the results of this experiment showed that while the addition of bFGF and EGF caused a significant induction of ³H-Thymidine uptake by the bovine vascular endothilium cells, thus indicating a significant activation of the cells, the addition of melanotropin to the same cells had no effect.

The combined results of Examples 1 to 3 show the selectivity of the effect of melanotropin on activation of RPE cells as compared to human fibroblast and bovine vascular endothilium cells.

EXAMPLE 4

The effect of melanotropin on the migration of RPE cells

The ability of RPE cells to proliferate and migrate over denuded areas was measured using a slight modification of the previously known technique termed "wound closure technique" (Jumblatt and Neufeld, 1986).

In this example bovine RPE cells were grown as described in Example 1 and plated in microwell plates containing 16 ml wells. When the cultures reached confluency, sloughing of the cells from a centrally located area in each well was carried out using a very sharp blade. In order to remove non adherent cells, each well was rinsed with a 1 ml Earle's balanced salt solution (EBSS: Gibco). The cultures were photographed at the time of the sloughing and at 12, 24 and 48 hours after the sloughing procedure. In this way the size of the denuded area in the culture at the time of the sloughing was documented and could be compared later to the same cultures at different time periods after the denudation.

The ability of the bovine RPE cells to proliferate and migrate over the denuded area in the well was determined by analyzing the covered and uncovered area in the photographs of the cultures taken at different time periods as described in Jumblatt & Neufeld (ibid). The rate of the "wound" closure was calculated as $mm^2$ per hour or as the percentage of the covered area in the culture wells at a specific time period.

The bovine RPE cell cultures were divided into six groups. To each group different factors were added to the growth medium immediately after the "wounding" and rinsing procedures were completed. The medium added to each of the six groups of bovine RPE cell cultures was as follows: (1) growth medium alone; (2) growth medium containing $10^{-10}$ mg/ml of bFGF; (3) growth medium containing $10^{-6}M$ melanotropin; (4) growth medium containing $10^{-7}M$ melanotropin; (5) growth medium containing $10^{-8}M$ melanotropin; and (6) growth medium containing $10^{-9}M$ melanotropin.

The migration of single cells at the margin of the wound area was first noted twelve hours after the wounding by using the phase contrast microscope. In the course of migration, the cells lost their polygonal configuration and assumed a spindle-shaped elongated appearance or some other polymorphus shape. The results are summarized in the following FIGS. 3 and 4.

Figure 3:
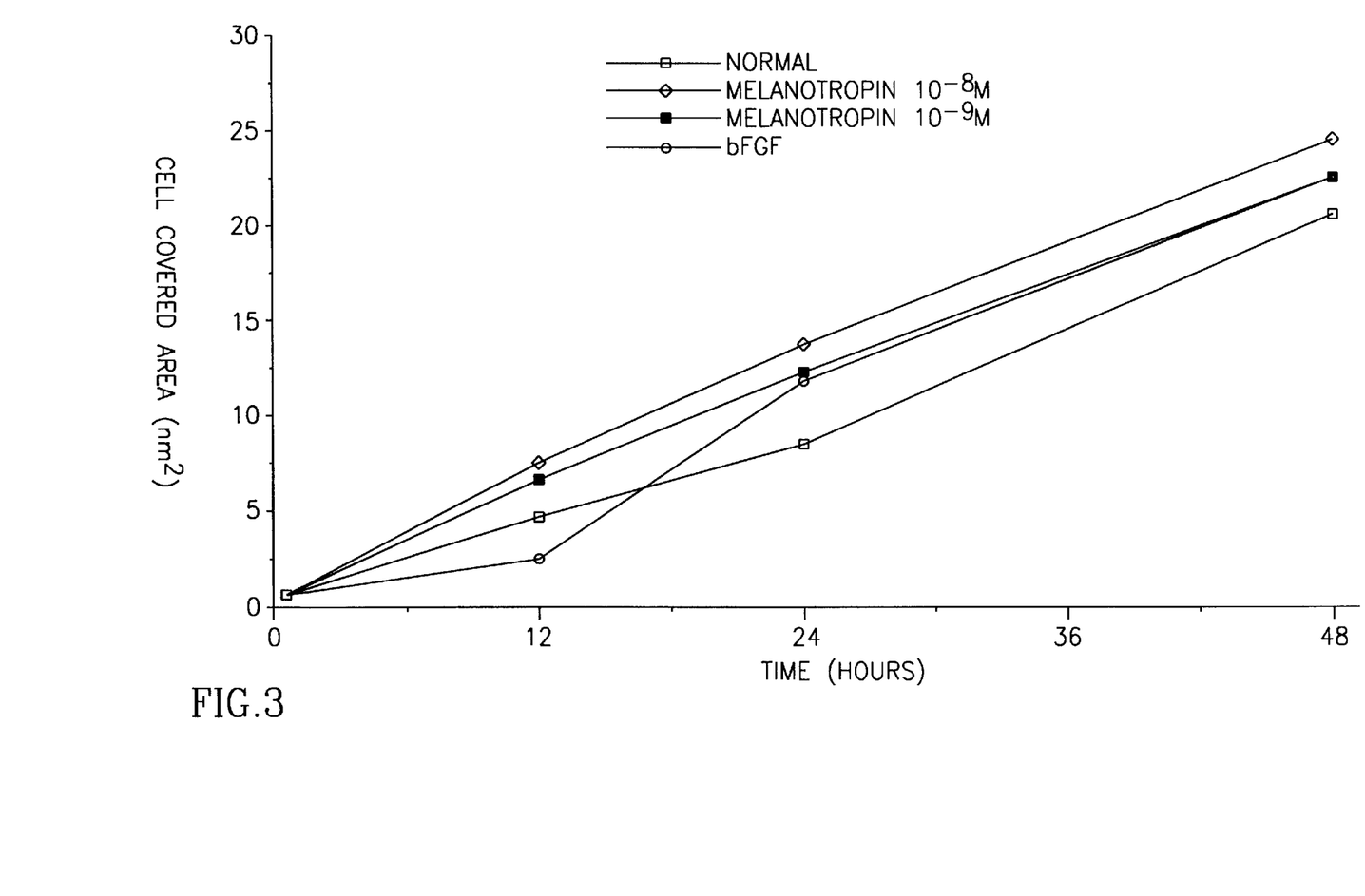
FIG. 3 shows the area (mm$^2$) covered by RPE cells in four bovine RPE cell cultures, each incubated with a medium containing a different growth factor or different concentrations of the growth factor: melanotropin $10^{-8}$M, melanotropin $10^{-9}$M, bFGF and a control medium. The area was measured at various time periods after sloughing of the cells from a centrally located area in the well.
Figure 4:
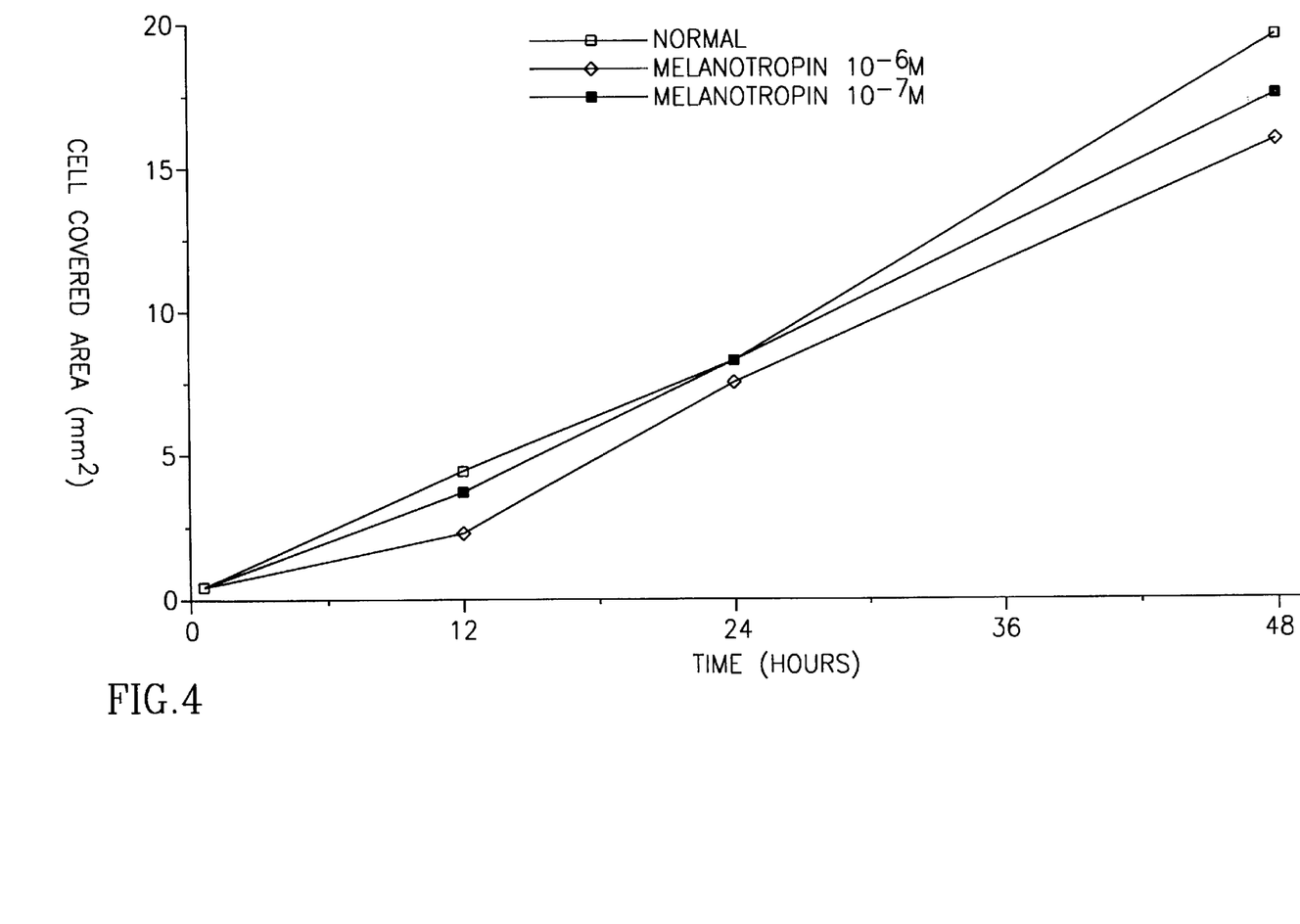
FIG. 4 shows the area (mm$^2$) covered by RPE cells in 3 bovine RPE cell cultures each incubated with a growth medium containing a different growth factor or different concentrations of the g.f.: melanotropin $10^{-6}$M, melanotropin $10^{-7}$M and a control medium at different time periods after the sloughing of the cells from a centrally located area in the well.

As seen in FIGS. 3 and 4, the most pronounced increase in cell proliferation and migration, as measured by the area covered by the RPE cells in the culture wells, occurred 48 hours after the wounding process. At this time period the covered area was about twice larger than the covered area observed at 12 hours of the respective culture well.

12 hours after the wounding process and addition of bFGF to the RPE cells, the size of the cell covered area in the wells treated with bFGF was not significantly larger than the covered area in the wells of the cells treated with growth medium alone ($11.4 \pm 1.1$ $mm^2$ as compared to $8.0 \pm 1.0$ $mm^2$).

However, 48 hours after the addition of bFGF to the cultured medium of the RPE cells, the covered area in the culture was significantly larger as compared to the covered area observed in the RPE cell culture treated with conditioned medium alone ($21.1 \pm 0.7$ $mm^2$ as compared to $19.8 \pm 0.8$ $mm^2$, $p<0.05$).

The effect of melanotropin on the proliferation and migration of the RPE cells was dose dependent. The area covered by RPE cells in the wells treated with $10^{-6}M$ of melanotropin was significantly smaller than the covered area observed in wells treated with $10^{-7}M$ melanotropin ($15.6 \pm 1.5$ $mm^2$ in wells treated with $10^{-6}M$ as compared to $19.8 \pm 0.8$ $mm^2$ in wells treated with $10^{-7}M$, $p<0.05$). High concentrations ($10^{-6}M$ and $10^{-7}M$) of melanotropin had no effect on the size of the area covered by the cells as compared to wells treated with the conditioned medium alone. Thus, addition of melanotropin in the high concentrations did not affect the ability of the RPE cells to proliferate and migrate.

However, addition of the melanotropin in lower concentrations ($10^{-8}M$ and $10^{-9}M$) to the wells increased the cell covered area of these wells as compared to the cell covered area in the wells of the cells treated with conditioned medium alone, both at 24 hours and at 48 hours after the wounding process. The size of the covered area in the melanotropin treated wells was about 1.5 fold higher than the size of the covered area in the wells of the cells treated with conditioned medium alone. The effect of low concentrations of melanotropin on the proliferation and migration capacity of the RPE cells was therefore dose dependent and similar to that of bFGF.

EXAMPLE 5

The effect of melanotropin on the intraocular pressure (IOP) in rabbits

Pigmented rabbits of either sex, weighing 2 to 3.5 kg. were maintained in standard cages with free access to food and water in a temperature controlled room and were exposed to a light-dark cycle of 12 hours, i.e. 12 hours of light followed by 12 hours of darkness, etc.

Intraocular pressure (IOP) was measured using a Digilab Model 30R Pneumatonometer. The readings were matched with 3-point standard pressure readings performed daily using a Digilab Calibration Verifier. All IOP measurements were carried out by the same operator using the same tonometer. Immediately before each series of IOP measurements, one drop of a local anesthetic (Localin-Benoxinate HCl 0.4%, Fischer Pharmaceuticals, Israel) was instilled in each eye. The animals were accustomed to the experimental procedure by repeated handling. Rabbits that showed a consistent difference in IOP between the eyes or any sign of ocular irritation during the period of acclimatization and baseline measurements, were excluded from the study. The average IOP of both eyes, measured at each time point was recorded as one value.

Since IOP values are known to fluctuate during various time intervals and at different hours of the day, a "baseline IOP curve" was determined for each rabbit on the day preceding the experiment. The baseline curve was determined by measuring the IOP of the rabbit over a period of six hours starting at 08.00 in the morning and until 14.00 the same day at hourly intervals.

The animals were divided into three groups (7 rabbits per group) which received the following treatments: (1) a subcutaneous (S.C.) injection of 1 ml sterile saline (control group); (2) a subcutaneous injection of 2 mg/kg of melanotropin; and (3) a subcutaneous injection of 10 mg/kg of melanotropin.

The IOP values were measured at the same hours of the day at which the baseline measurements were carried out the day before. Rabbits were not used in more than two experiments, with the minimum of 10 days separating between two consecutive experiments.

Figure 5:
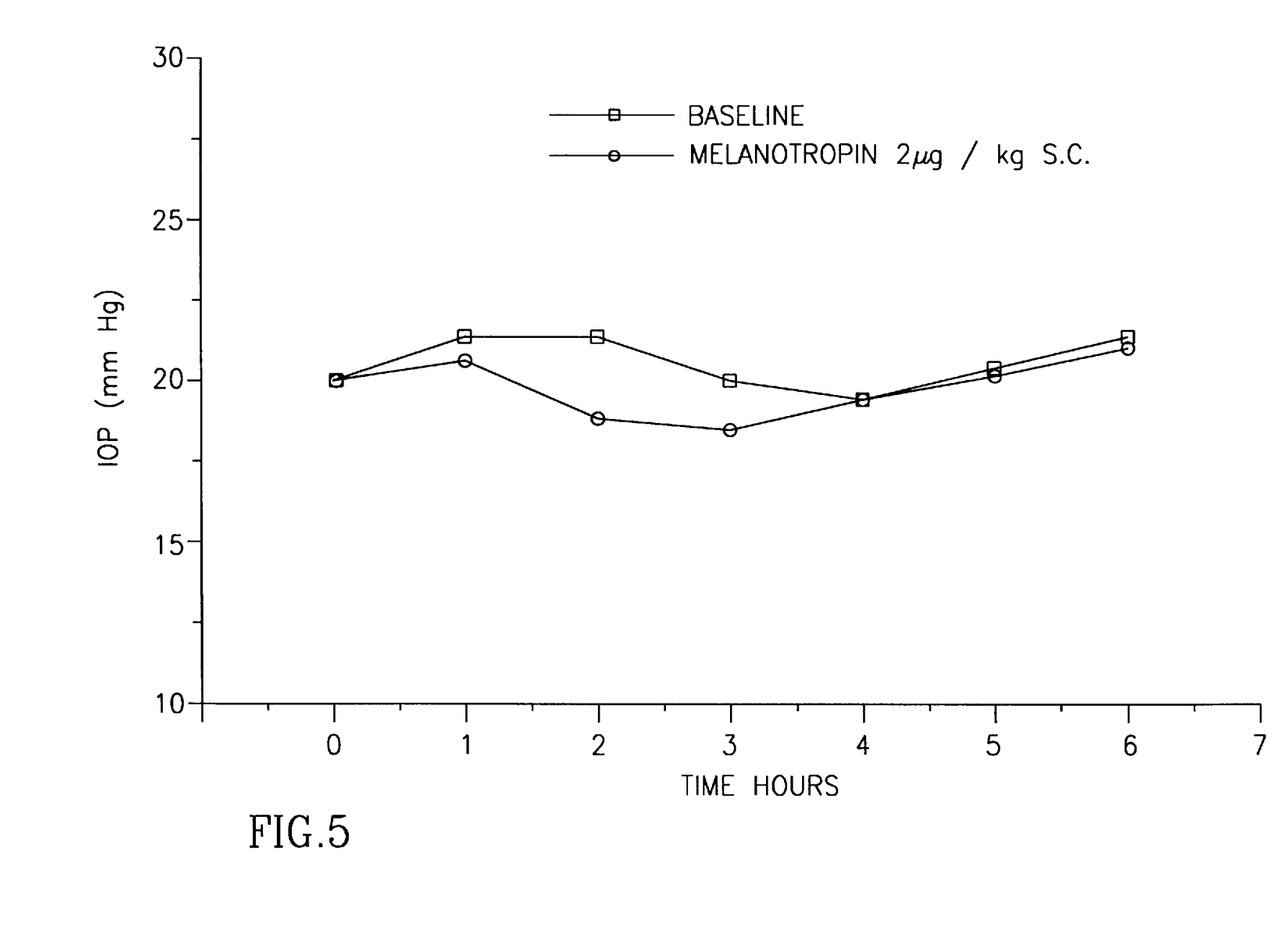
FIG. 5 shows the intraocular pressure (IOP) in mm/Hg in rabbits from two experimental groups, one group injected subcutaneously with sterile saline and the other group injected subcutaneously with 2 μg/kg. of melanotropin as measured at different time periods after the subcutane injection.
Figure 6:
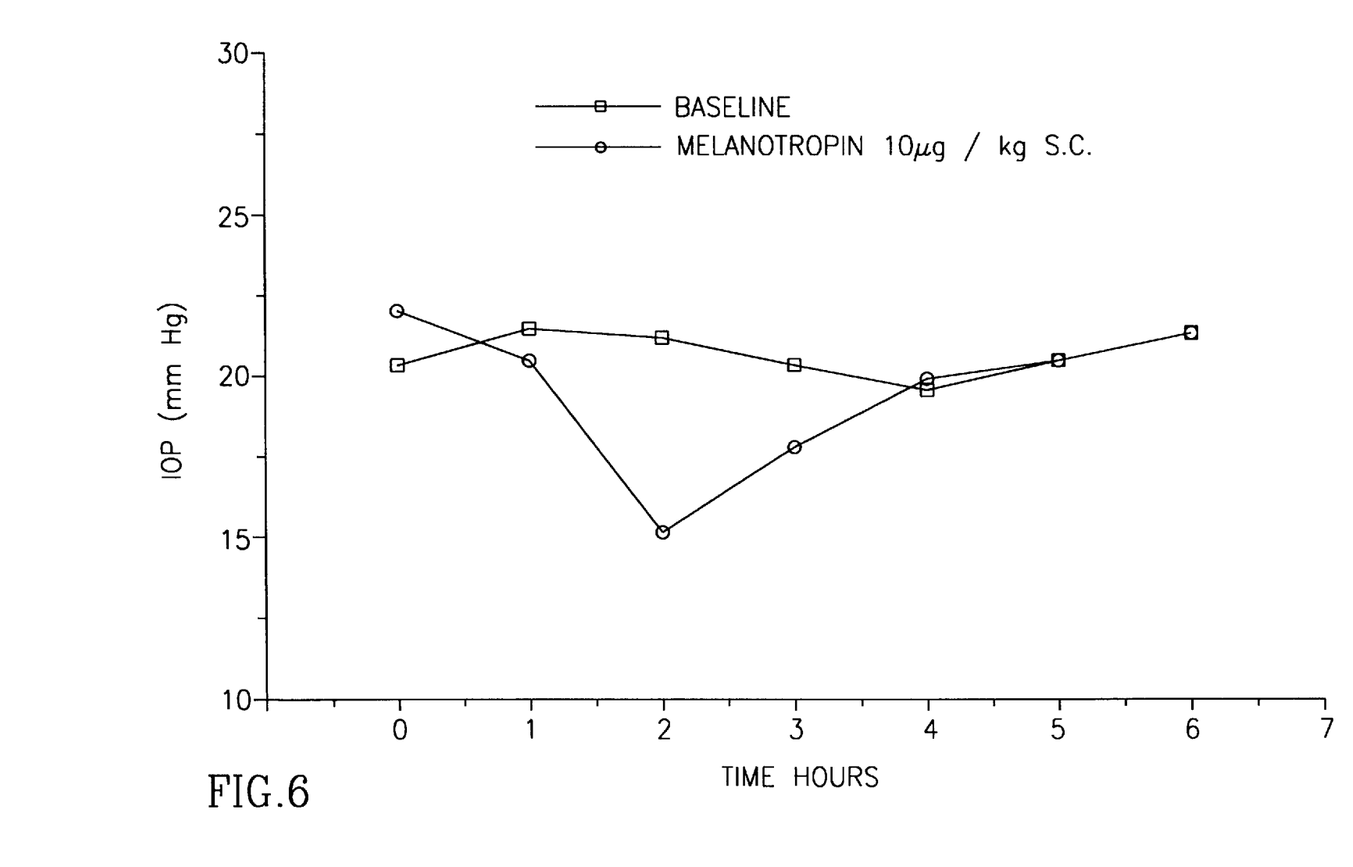
FIG. 6 shows the intraocular pressure (IOP) in millimeters Hg in rabbits from two experimental groups, one group subcutaneously injected with sterile saline and the other group subcutaneously injected with 10 μg/kg of melanotropin as measured at different time periods after the subcutane injection.

The results seen in FIGS. 5 and 6 are mean±S.E. of rabbits of each treatment group. Students' t tests was used to calculate the significance of differences between different treatment groups. Each measurement of IOP was compared to the measurement of the IOP at the same time of day before the treatment.

As seen in FIGS. 5 and 6, there were no significant differences in the IOP level of the various experimental and control groups at time zero of the experiment (i.e. before the animals were treated), indicating the reproducibility and reliability of this method.

However, rabbits' IOP measured after melanotropin treatment was significantly lower than the IOP measured in the rabbits of the control group (p<0.01) with maximal values two hours after the treatment. There was only a 10% decrease in the IOP level in rabbits treated with 2 mg/kg of melanotropin as compared to the IOP of the same rabbits before receiving the treatment at the same hour of the day. In the rabbits receiving 10 mg/kg of melanotropin, the decrease in the IOP was significantly higher and reached 30% as compared to the corresponding baseline value. Such a significant effect on the IOP level is similar to the effect of Pilocarpine or Tab. Diamox both of which are potent antiglaucoma medications.

These results show that melanotropin exerts a significant dose related effect on reducing the IOP of treated rabbits and might be of clinical significance.

EXAMPLE 6

The effect of melanotropin on $LTB_4$ production (a parameter for inflammation) in the corneas of rats exposed to UV irradiation The antinflammatory activity of melanotropin in the eye was measured by the ability of the melanotropin to inhibit the production of the leukotriene ($LTB_4$) which is produced during the inflammatory response elicited by noxious stimulae to the cornea.

The ability of melanotropin to inhibit an inflammatory response was determined in corneas of albino rats subjected to UV irradiation. The parameter used to measure the inflammatory response was the amount of production of leukotriene B4—known for its modulatory action in inflammation.

One eye of albino rats of either sex weighing 200–250 gm was exposed to UV irradiation (200–400 nm) for 15 min. daily for 4 consecutive days. The other contralateral eye of each rat was not exposed to the irradiation and served as a control.

The animals were divided into three groups (8 rats in each group) as follows: (1) untreated; (2) rabbits exposed to UV irradiation and a daily intermuscular (i.m.) injection of 4 mg/kg dexamethasone; and (3) rabbits exposed to UV irradiation and treated with a daily injection (i.m.) of 10 μg/kg of melanotropin.

In the treated group of animals, the specific treatment began each day within one hour after the UV exposure. The animals were sacrificed two days following the last UV irradiation and the eyes were frozen at −70° C. The cornea was disected and incubated in a shaking bath at 37° C. for 40 mins. in a Heppes buffer (pH=7.4). At the end of the incubation, a sample was obtained from the medium and the contents of the leukotrien $B_4$ ($LTB_4$) was determined by a radioimmunoassay (RIA) technique using a New England Nuclear Kit with a specific antibody against $LTB_4$.

Figure 7A:
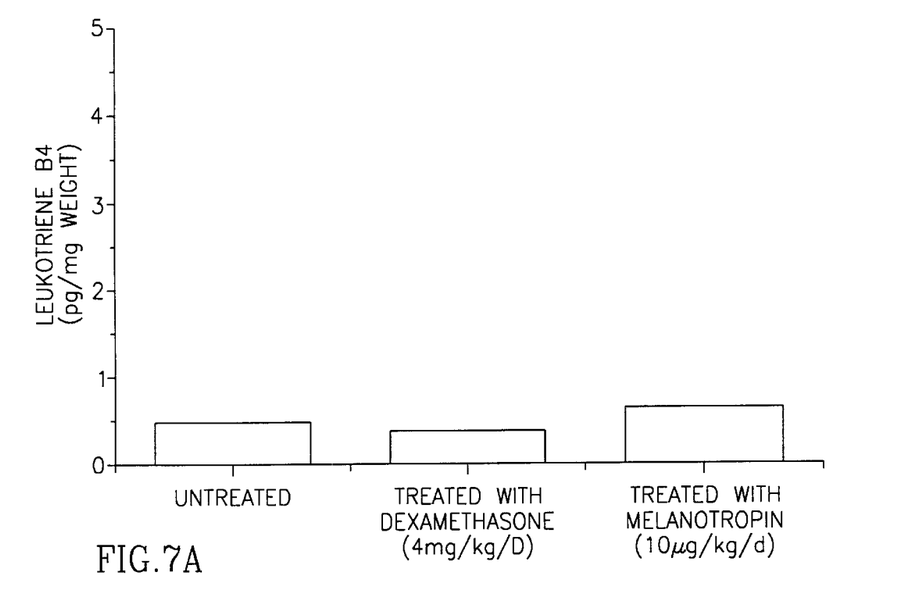

As seen in FIG. 7(a), there were no differences in the leukotriene B4 concentration in the medium containing corneas of the eyes of rats from the three experimental groups which were not exposed to UV irradiation. (The $LTB_4$ level in all 3 groups was 0.51±0.29 pg/mg).

Figure 7B:
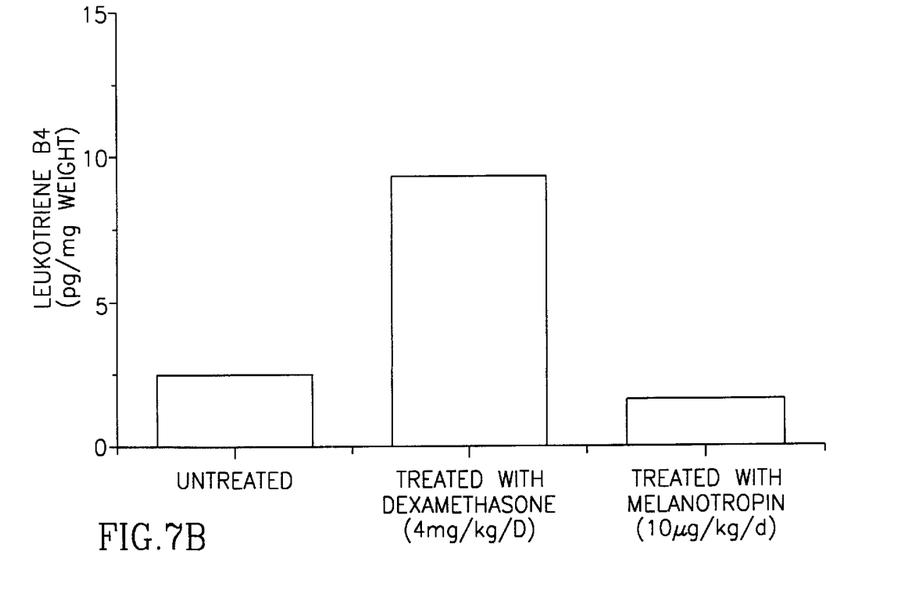

FIGS. 7(b) shows that following UV irradiation there was a significant increase in $LTB_4$ production by the cornea reaching 2.47±0.8 pg/mg which is about 5 times higher than the amount of the $LTB_4$ in the non irradiated contralateral eye (p=0.001). As can further be seen in FIG. 7(b), the treatment of the UV irradiated eye with 4 mg/kg per day of dexamethasone significantly increased the production of $LTB_4$ in these corneas as compared to irradiated but untreated rats' corneas (9.38±2.4 pg/mg weight as compared to 2.47±0.8 pg/mg weight).

Treatment with melanotropin caused a reduction in the amount of $LTB_4$ produced by the corneas of the UV irradiated eyes as compared to the amount produced by the corresponding irradiated untreated rats' corneas (1.6±0.5 pg/mg weight as compared to 2.47±0.8 pg/mg weight, p<0.05).

The production of prostaglandin type $E_2$ ($PGE_2$) was also measured in the eyes of three groups of rats. The amount of $PGE_2$ in the eyes exposed to UV irradiation was higher than in the nonirradiated control eyes (4.1±1.9 pg/mg weight as compared to 1.8±0.3 pg/mg weight, p=0.001).

Figure 8A:
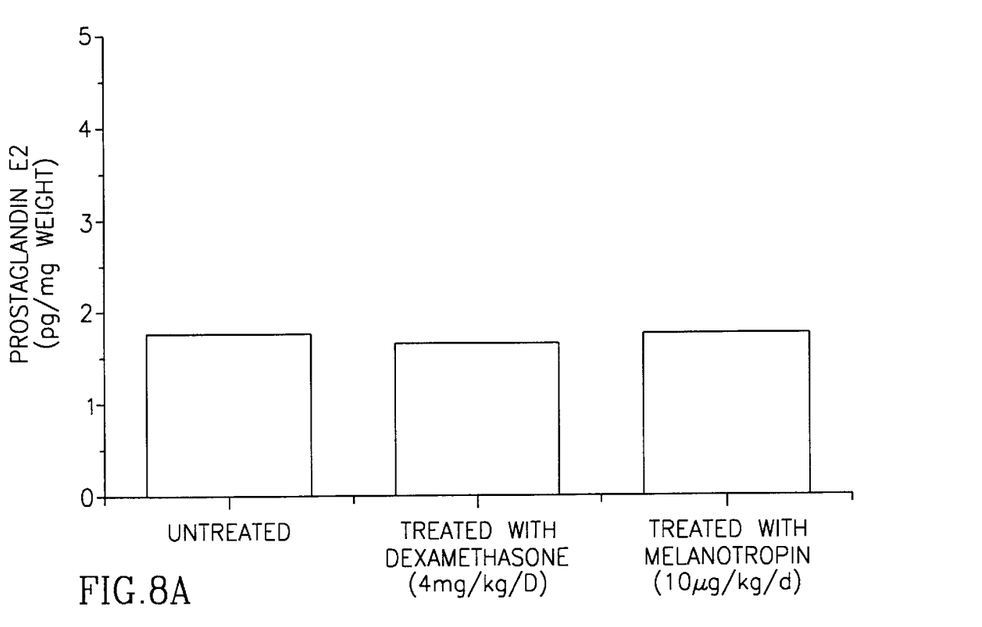
Figure 8B:
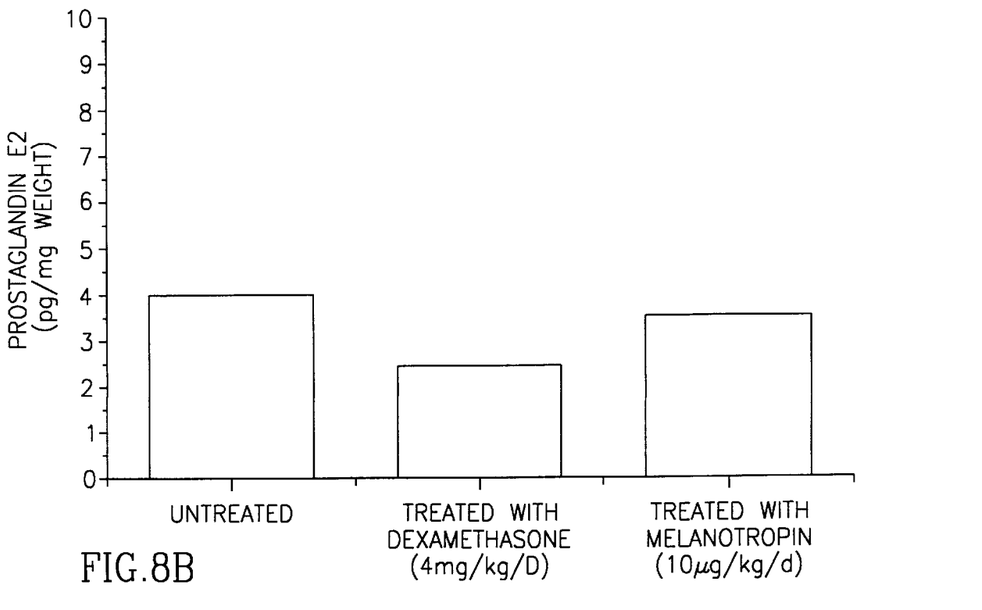

As seen in FIG. 8(b) the amount of $PGE_2$ produced by UV irradiated corneas and treated with dexamethasone was lower than the amount of the $PGE_2$ in the irradiated but untreated rats' corneas. The level of $PGE_2$ produced following UV irradiation and treatment with 10 μg per day of melanotropin was not significantly reduced as compared to that produced in rats' corneas following UV irradiation alone.

These results show that treatment with melanotropin may inhibit $LTB_4$ production in the noninflamed eye and therefore melanotropin may act as an anti-inflammatory agent. These results also show that the effect of melanotropin on $LTB_4$ production is at least partially specific since $PGE_2$ levels for example, were not effected by the treatment with melanotropin.

REFERENCES

1. Hanoaka, T., Effect of melanophone hormone on regeneration of visual purple in solution, Nature, 170, 866 (1953).
2. Stroeva, O. G. and Bibikova, A. D., A hormone-sensitive stage in development of the retinal pigment epithelium in Hunter rats with inherited retinal dystrophy, Ontogenez, 19, 30–36 (1988).
3. Bauer, B. and Ehringer, B., Action of A-MSH on the release of neurotransmitters from the retina, Acta. Physiol. Scand., 108, 105–107 (1980).
4. Bar-Ilan, A., Weissman, C., Savion, N and Naveh N., Alpha melanocyte stimulating hormone (α-MSH) enhances eicosanoid production by bovine refined pigment epithelium, Prostglandins, 43 31–34 (1992).
5. Dayes, R. A., et al., Journal of Immunology, 139(1), 103–109 (1987).
6. Sawyer, T. K., et al, Peptides, 11, 351–357 (1990).
7. Baird, A., Esch, F., Gospodorowicz, D., Guillemin, R., Retinal derived endothelial ccll growth factors, Biochemistry, 24, 7859 (1985).
8. Benelli, A, Zanoli, P., Botticelli, A. and Bertolini, A [$Nle^4$D-$Phe^7$] α-MSH improves functional recovery in rats subjected to diencephalic hemisection, Europ. J. Pharm., 150, 211–219, (1988).
9. Johnston, M. F., Kravitz, E. A., Meiri, H. and Rahamimoff, Aurenocorticotropic Hormone Causes Long-Lasting Potentiation of Transmitter Release from Frog Motor Nerve Terminals, Science, 220, 1071–1072, (1983).
10. Hadley, Mac E. and Dawson, B. V., Biomedical Applications of Synthetic Melanotropins, Pigment Cell Research, Supplement 1, 69–78, (1988).

I claim:

1. A method for the treatment or prevention of diseases or disorders of the eye, the diseases or disorders being inflammatory reactions or diseases or disorders associated with increased intraocular pressure (IOP), comprising administering to a subject an effective amount of an active agent being a melanotropin peptide or an analog thereof, said analog being selected from the group consisting of agents which are capable of binding to melanotropin peptides' receptors, agents capable of increasing the level of a second messenger of such receptors, and an agent capable of mimicking or modulating the activation of the target of said second messenger.

2. A method according to claim 1, wherein said melanotropin peptide is selected from the group consisting of α-MSH, β-MSH, γ-MSH, lipotropins of the β and γ type and melanocytic concentrating hormone (MCH).

3. A method according to claim 1, wherein said active agent is α-MSh or Nle$^4$D-Phe$^7$ α-MSH.

4. A method according to claim 1, wherein said active agent is administered topically on the eye.

5. A method according to claim 1, wherein said active agent is administered systemically.

6. A method for promoting an anti-inflammatory response to non-specific inflammatory reaction within the eye of an individual, comprising administering to the individual, either topically on the eye or systemically, an effective amount of an active agent selected from the group consisting of α-MSH, β-MSH, γ-MSH, lipotropins of the β or γ type, melanocytic concentrating hormone (MCH) and Nle$^4$D-Phe$^7$ α-MSH.

7. The method according to claim 6, wherein said active agent is administered topically on the eye.

8. The method according to claim 6, wherein said inflammatory reaction is associated with change in the level of leukotrienes or prostaglandins in inflamed cells.

9. The method according to claim 7, wherein said inflammatory reaction is associated with changes in the level of leukotrine $B_4$ or protstaglandin $E_2$ ($PGE_2$) in inflamed cells.

10. A method for the treatment of eye diseases or disorders associated with increased intraocular pressure (IOP), comprising administering to a subject an effective amount of an active agent selected from the group consisting of α-MSH, β-MSH, γ-MSH, lipotropins of the β and γ type, melanocytic concentrating hormones (MCH) and Nle$^4$D-Phe$^7$ α-MSH.

11. The method according to claim 6, wherein said active agent is α-MSH or Nle$^4$ D-Phe$^7$ α-MSH.

12. The method according to claim 6, wherein said active agent is administered systemically.

13. The method according to claim 10, wherein said active agent is α-MSH or Nle$^4$ D-Phe$^7$ α-MSH.

14. The method according to claim 10, wherein said active agent is administered systemically.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 13 Amino Acids
        ( B ) TYPE: Amino Acid Chain
        ( C ) STRANDEDNESS: Single
        ( D ) TOPOLOGY: Linear     ( i i ) MOLECULE TYPE: Peptide     ( i i i ) HYPOTHETICAL:

( i v ) ANTI-SENSE:

( v i ) ORIGINAL SOURCE:
        ( A ) ORGANISM:
        ( C ) INDIVIDUAL ISOLATE:
        ( G ) CELL TYPE:

( v i i ) IMMEDIATE SOURCE:
        ( A ) LIBRARY:
        ( B ) CLONE:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( K ) RELEVANT RESIDUES IN SEQ ID NO:

( x i ) SEQUENCE DESCRIPTION: SEQ ID NO: 1:

Ser Tyr Ser Met Glu His Phe Arg Trp Gly Lys Pro Val
                  5                        10